United States Patent [19]

Laurent et al.

[11] Patent Number: 5,007,733
[45] Date of Patent: Apr. 16, 1991

[54] PROCESS AND DEVICE FOR DETERMINING THE CLOUD POINT OF A DIESEL OIL

[75] Inventors: Dominque Laurent; Gerard Fortunato, both of Lyons; Bernard Damin, Oullins; Marcel Napoleon, St Verges Mepieu Montalieu Vercieu, all of France

[73] Assignee: Elf France, Paris, France

[21] Appl. No.: 742,580

[22] Filed: Jun. 7, 1985

[30] Foreign Application Priority Data

Jun. 12, 1984 [FR] France ................................. 84 9127

[51] Int. Cl.$^5$ .................................................. G01N 33/28
[52] U.S. Cl. ........................................... 356/70; 356/338
[58] Field of Search ................ 356/70, 337, 338, 36, 356/37; 374/17

[56] References Cited

U.S. PATENT DOCUMENTS

| | | | |
|---|---|---|---|
| 3,031,880 | 5/1962 | Findlay | 374/17 |
| 3,457,772 | 7/1969 | Chassagne et al. | 374/17 |
| 3,999,855 | 12/1976 | Hirschfeld | 356/338 |
| 4,072,421 | 2/1978 | Coyne et al. | 356/338 |
| 4,152,070 | 5/1979 | Kushner et al. | 356/442 |
| 4,377,001 | 3/1983 | Takeda et al. | 374/17 |

OTHER PUBLICATIONS

"An Instrument for the Measurement of Spectral Attenuation Coefficient and Narrow Angle Scattering Funchon of Ocean Waters" Austin et al. *SPIE*, vol. 64, Ocean Optics 1973, pp. 50–61.

*Primary Examiner*—Richard A. Rosenberger
*Attorney, Agent, or Firm*—Burgess, Ryan & Wayne

[57] ABSTRACT

The present invention concerns a process and a device for determining the cloud point of a diesel oil, comprising a light source and, aligned on a single axis, a diaphragm comprising a central hole on the said axis, an objective forming the image of the hole on a light trap, and behind the screen, a wide-diameter photoelectric detector intended to deliver an electric current when it receives a light flux, and, disposed between the objective and the screen, a cell containing a diesel oil sample to be analyzed, means for controlling the temperature of this sample being associated to the said cell.

4 Claims, 2 Drawing Sheets

PROCESS AND DEVICE FOR DETERMINING THE CLOUD POINT OF A DIESEL OIL

FIELD OF THE INVENTION

Background of the Invention

The present invention concerns a process for determining the cloud or turbidity point of a gas oil or a diesel oil and it results partially from the studies carried out at Institut d'Optique Théorique et Appliquée by Jacques VULMIERE. It also concerns a device for carrying out this process.

Various processes and devices for determining the cloud point of diesel oil have been proposed up to now. By cloud point is meant the temperature at which and below which crystals appear in the diesel oil, during its cooling.

These processes are essentially based upon the rapid change of the optical properties of the diesel oil at cloud point, and utilize either a depolarization phenomenon of an initially polarized light beam, after it has through-crossed a liquid sample in which the crystals appear, or the diffusion of a light beam in a sample during formation of the crystals, the temperature of the sample being, in every case, controlled and progressively lowered until the change of the optical properties is observed.

SUMMARY OF THE INVENTION

The present invention provides a process allowing a rapid and accurate determination of the cloud point.

This process presents, furthermore, the advantage of being able to be carried out with a simple and reliable device, and of supplying results offering a good correlation with the visual method conventionally utilized.

The process according to the invention for determining the cloud point of a diesel oil, in which is utilized the scattering of light by a disel oil sample when the paraffinic crystals begin to form, consists in focussing on a screen absorbing the whole of the image of a light source through a cell containing the said diesel oil sample maintained at a temperature higher than the cloud point, then in progressively lowering the temperature of the sample of the diesel oil, in collecting on a large-surface photoelectric detector disposed behind the screen, the luminous flux diffused by the sample when the temperature of said sample reaches cloud point and in observing the increase of the current supplied by this detector in function of the temperature decrease of the sample.

For carrying out this process, the invention provides, furthermore, a device comprising a light source and, aligned on a single axis, a diaphragm comprising a central hole on the said axis, an objective forming the image of the hole on a light trap, and behind this screen, a large-diameter photoelectric detector adapted to deliver an electric current when it receives a light flux and, disposed between the objective and the screen, a cell containing a diesel oil sample to be analyzed, and means for adjusting the temperature of this sample.

BRIEF DESCRIPTION OF THE DRAWINGS

The objects, features and advantages of the present invention will become more apparent from the following description, given by way of non-limitative illustration, with reference to the appended drawings in which.

DETAILED DESCRIPTION OF THE DRAWINGS

Figure 1:
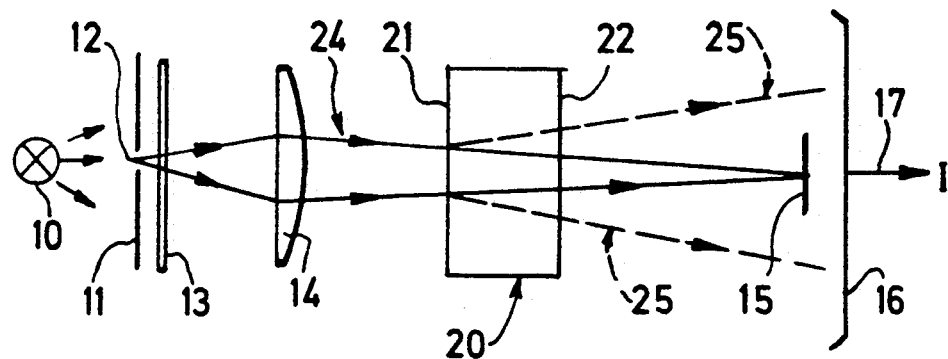
FIG. 1 illustrates schematically the device for carrying out the process according to the invention.

The device according to the invention is schematized in FIG. 1. It comprises a light source 10, for example, iodine quartz lamp, and successively, aligned on a single axis, a diaphragm 11 comprising a central hole 12 on the said axis, this hole 12 having a reduced diameter, for example 2 mm, an interferential filter 13, an objective lens 14 forming the image of hole 12 on an opaque screen 15, constituting a light trap, and behind this screen, a large diameter photoelectric detector 16, adapted to supply a current I, at 17, when it receives a luminous flux.

A cell 20 containing the diesel oil to be analyzed is disposed between the objective lens 14 and the screen 15; this cell the structure of which is described in further detail herein-below, comprises on the path of the light beam 24 issuing from objective lens 14, two windows 21 and 22 having parallel faces and which do not deflect this beam.

When the diesel oil contained in tank 20 does not comprise crystals, all the light issuing from the source 10, more precisely from hole 12, is received and stopped by opaque screen 15. Detector 16, that does not receive any light, delivers at 17 a zero or substantially zero current.

Upon the formation of crystals within the diesel oil, the light is scattered in the zone of the cell (rays 25) and impinges on the sensitive part of the detector 16, not masked by the screen 15, this detector thus delivering a current I, this latter increasing very rapidly as a function of the decrease of temperature.

This rapid current increase allows to measure with a sufficient accuracy, (of about $\frac{1}{4}°$ C.), the temperature at which cyrstals appear in the diesel oil. The same current is advantageously utilized for the cooling of cell 20, as will be seen herein-below.

Figure 2:
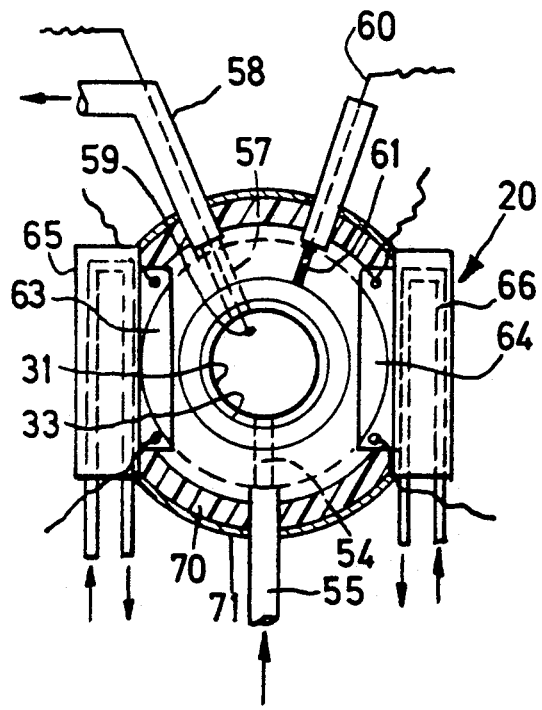
FIGS. 2 and 3 are two views of a cell equipping the device according to the invention, respectively in cross-section and in axial section.
Figure 3:
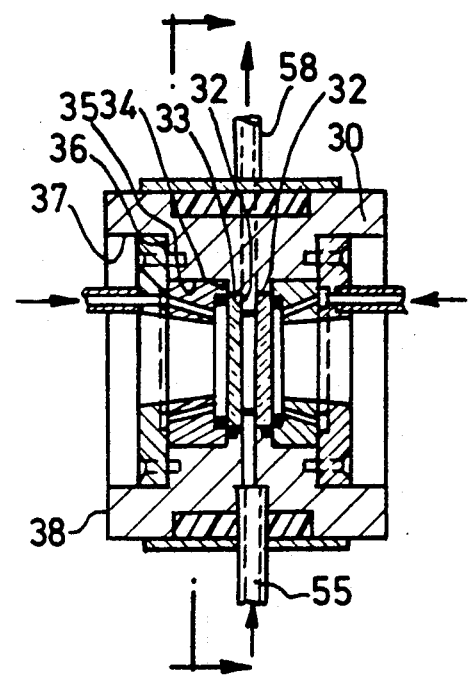
Figure 4:
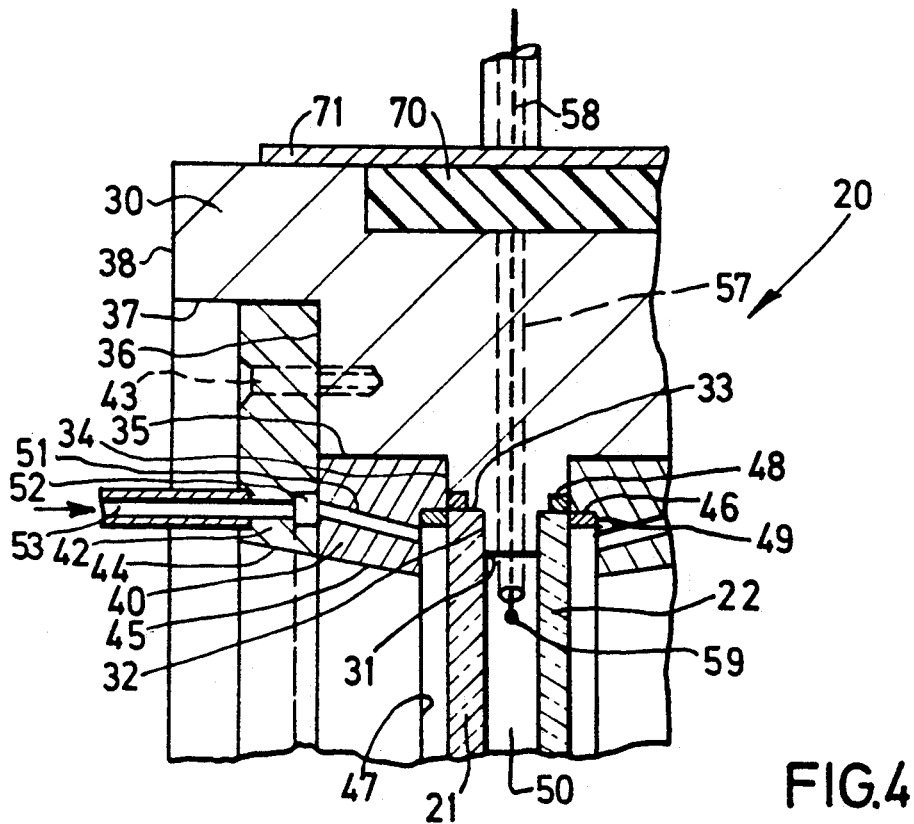
FIG. 4 is a partial view, on a larger scale, of the cell represented in FIG. 3.

Cell 20 in the embodiment represented in FIGS. 2 and 3 and, partially, on a greater scale in FIG. 4, consists of a metallic body 30 having a generally cylindrical form, along the axis of which is provided a central passage. This central passage that cross body 30 is symmetrical with respect to the symmetry plane of this body, which is perpendicular to the axis of said body. It comprises, starting from a central bore 31, on either side of said bore, a succession of concentric annular bearing surfaces 32, 34, 36, 38 that connect bores of increasing diameters 33 35, 37. Bearing surface 38 constitutes the external face of body 30. FIG. 4 illustrates in detail this deposition for the left-hand side of the body, as an axial view, the same disposition being symmetrically repeated for the right-hand side part.

The innermost bearing surfaces 32, receive the circular transparent window elements 21, 22 having parallel faces, that constitute the windows of the cell 20, and have a diameter slightly smaller than that of the bore 33. Each window element is maintained in place by a ring 40, the diameter of which corresponds to that of the bore 35, and which is housed within this bore, the depth of which corresponds to the thickness of the ring 40. In turn, each ring 40 is retained by a washer 42, having a diameter corresponding to that of the bore 37 and housed within said bore, the internal face of this washer resting on the external face of the ring 40. Means are provided for pushing the washer 42 against the bearing surface 36, for example screws 43.

The internal bores 44 and 45 of washer 42 and ring 40, respectively form a passage which leaves free a major part of each transparent window element 21, 22.

An annular step 46 is provided in the internal face of the ring 40, opposite the adjacent window element, and provides on this face a bearing surface 47, spaced apart from the said blade. Sealing rings 48, 49 are disposed around these window elements 21, 22 and between them and the rings 40, in order to provide between these window elements a sealed chamber 50.

In each ring 40, are provided a series of passages 51, through-crossing the said ring and issuing by an end on the bearing surface 47, whereas in the internal face of washer 42 is provided an annular groove, forming a collector, into which issues the other ends of the passages 51. A duct 53, connected to an air source (not represented) through-crosses the washer 42 and issues into groove 52. By blowing pressurized air through channel 53, air jets are projected onto the external faces of window elements 21, 22 for cleaning the same when required.

A channel 54 connected by a duct 55 admitting the diesel oil to be analyzed is provided within the thickness of body 30 and issues into chamber 50 and a passage 57 also provided in body 30 and issuing into chamber 50, substantially opposite the previous one, is connected to a diesel oil evacuation channel 58.

A thermoelectric sensor 59 is disposed in passage 57, its sensitive element being placed inside chamber 50, in order to measure the temperature of the diesel oil in the said chamber.

Another sensor 61, housed in a blind hole 60 provided in body 30, allows to measure the temperature of this body.

In symmetrically disposed housing of body 30, adjacent to chamber 50, are disposed two Peltier elements 63, 64 each of which is associated to a radiator 65, 66, respectively, with internal water circulation in order evacuate the heat or cold produced in said elements.

Furthermore, for an improved calorifuging of the cell, an insulating layer 70, for example polystyrene foam, is injected between the wall of the cell and a protective coating 71.

The current delivered by detector 17 upon the appearance of clouding in the diesel oil in chamber 50 is utilized to control the thermal cycle of the Peltier elements 63, 64 cooling the cell 20, as well as for controlling the cycle of evacuation of the diesel oil from the cell once the measurement has been carried out.

The volume of chamber 50 is very small, thereby allowing a rapid variation of the temperature of the diesel oil that it contains and very short measuring times to be achieved.

Figure 5:
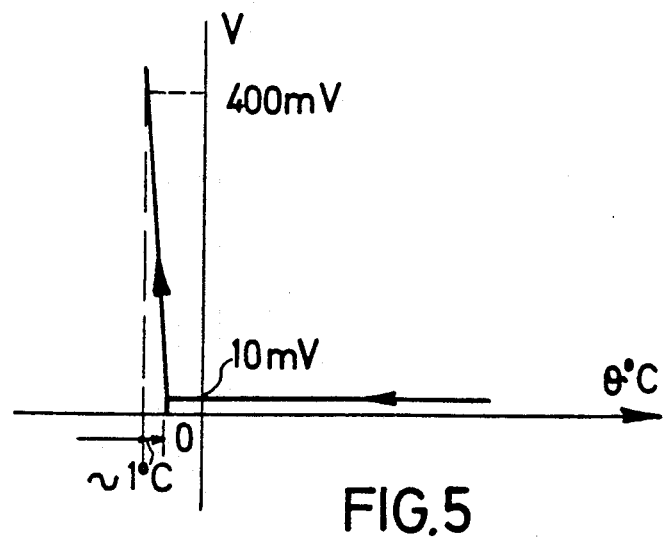
FIG. 5 is a diagram illustrating the variation of the current supplied by the detector of the device as function of the temperature of the diesel oil in the cell.

Furthermore, the constitution of the cell allows to operate with a clean optical system and to keep this system clean. The variation of current obtained between the time out which no crystals are present and the time of first appearance of said crystals is very close to a sudden non progressive on-off variation since the obscurity voltage (absence or crystals and light trapped by screen 15) is, for example, of 10 mV, whereas upon formation of said crystals and for a temperature variation of less than 1° C., this voltage increases to, for example, 400 mV (FIG. 5).

For a further improved efficiency, instead of constituting light trap 15 by a mat black screen, it is possible to utilize a Vulmière light trap (a reflecting cone, the apex of which is turned towards the light source) or a spherical mirror centered upon chamber 50. Similarly, interferential filter 13 can be replaced by a heat absorbing filter (adapted to stop the infra-red radiation which disturbs the measurements) or a coloured filter providing a more efficient exploitation of the senstivity of the detector. An interferential filter can, furthermore, combine these two effects.

It is to be noted that the process according to the invention is quite consistent with the visual method conventionally utilized, which is much less accurate and the carrying out of which requests a long time.

The process according to the invention can be particularly well adapted to the piloting of an installation for mixing diesel oils, with a view to producing a diesel oil that meets standard specifications.

It is well understood that the present invention is in no way limited to the embodiments described and represented herein-and can be modified in many respects by those skilled in the art without departing from the scope and spirit of the invention.

What is claimed is:

1. A device for determining a cloud point comprising:
   a directed light course having an optical axis;
   a diaphragm having a central hole aligned on the optical axis of the light source;
   lens means to focus a light beam emitted by the light source and delimited by the diaphragm onto a light-trapping means centered on the optical axis and having a predetermined cross-section sufficiently large to capture the entire focussed light beam;
   a light filter interposed between the diaphragm and the lens means;
   a test cell to receive diesel oil therein and wherein the test cell is defined by a chamber delimited by two opposite, parallel, planar, transparent walls disposed perpendicular to the optical axis of the light source;
      each of said walls comprising a planar window element of transparent material, the cell being provided with an inlet conduit and an outlet conduit for the diesel oil;
   photo-electric light-detecting means disposed downstream from the light-trapping means, with reference to the direction of propagation of the light beam, and having a light receiving zone of a size substantially larger than the cross section of the light trapping means, said photo-electric means being adapted to emit a signal when receiving scattered light which is not trapped by the light-trapping means; and
   means for adjusting the temperature of the diesel oil in the cell comprised of thermo-electric sensors for measuring the temperature of the diesel oil and the temperature of the material delimiting the cell, and Peltier elements equipped with radiators adapted to receive a flow of heat-exchange fluid and means of adjusting the temperature of the diesel oil in the cell, whereby the temperature of the diesel oil is adjusted at the instant when the photo-electric means receiving such scattered light represents the cloud point of the diesel oil in the cell.

2. The device according to claim 1, wherein the filter is a heat rejecting filter adapted to arrest infra-red radiation emitted by the light source.

3. The device according to claim 1, wherein the filter is a colored heat rejecting filter adapted to arrest infra-red radiation emitted by the light source.

4. The device according to claim 1, wherein the filter is an interference filter having heat rejecting and spectral filtration properties.

* * * * *